(12) United States Patent
Lang

(10) Patent No.: US 7,018,644 B2
(45) Date of Patent: Mar. 28, 2006

(54) LIQUID AIR FRESHENER AND INSECTICIDAL COMPOSITIONS AND DEVICE FOR USING SAME

(75) Inventor: Angus Lang, Hull (GB)

(73) Assignee: Reckitt Benckiser (UK) Limited, Slough (GB)

(*) Notice: Subject to any disclaimer, the term of this patent is extended or adjusted under 35 U.S.C. 154(b) by 0 days.

(21) Appl. No.: 10/210,691

(22) Filed: Jul. 31, 2002

(65) Prior Publication Data

US 2003/0108703 A1 Jun. 12, 2003

Related U.S. Application Data

(63) Continuation of application No. PCT/GB01/00304, filed on Jan. 26, 2001.

(30) Foreign Application Priority Data

Jan. 31, 2000 (GB) .................................. 0002124

(51) Int. Cl.
*A01N 25/34* (2006.01)
(52) U.S. Cl. ................ 424/409; 424/47; 424/78.08; 424/78.09; 424/78.18; 424/78.31; 424/405; 424/419; 523/122
(58) Field of Classification Search ............ 424/45–47, 424/78.08, 78.09, 78.18, 78.31, 405, 406, 424/409, 419; 523/122
See application file for complete search history.

(56) References Cited

U.S. PATENT DOCUMENTS

| 2,524,590 | A | * | 10/1950 | Boe ........................... 252/305 |
| 4,501,730 | A | * | 2/1985 | Torii et al. ................ 424/76.9 |
| 4,534,509 | A | | 8/1985 | Holzner |
| 4,634,614 | A | | 1/1987 | Holzner |
| 5,194,264 | A | * | 3/1993 | Van Tonder ................ 424/405 |
| 5,565,208 | A | * | 10/1996 | Vlasblom .................... 424/405 |
| 5,935,554 | A | * | 8/1999 | Tomlinson .................... 424/45 |
| 6,395,290 | B1 | * | 5/2002 | Brown ........................ 424/408 |

FOREIGN PATENT DOCUMENTS

| EP | 0 520 547 A2 | 12/1992 |
| GB | 2 230 447 A | 10/1990 |
| JP | 4-314780 | * 11/1992 |
| WO | WO 96/08425 A2 | 3/1996 |
| WO | WO 98/52622 A1 | 11/1998 |

* cited by examiner

*Primary Examiner*—Neil S. Levy
(74) *Attorney, Agent, or Firm*—Akin Gump Strauss Hauer & Feld, LLP

(57) ABSTRACT

A non-aqueous, single phase, non-thickened liquid air freshener or insecticidal composition having a flashpoint of greater than about 62° C. is provided. The composition contains: a) a polar solvent; b) up to about 10 wt % of a non-polar aliphatic hydrocarbon solvent; and c) a fragrance or an insecticide. The composition may be dispensed from a device having a chamber with at least one wall made of a material which enables a vapor of the composition to diffuse out of the chamber.

14 Claims, No Drawings

LIQUID AIR FRESHENER AND INSECTICIDAL COMPOSITIONS AND DEVICE FOR USING SAME

CROSS-REFERENCE TO RELATED APPLICATIONS

This application is a continuation of International Application No. PCT/GB01/00304, filed Jan. 26, 2001, which was published in the English language on Aug. 9, 2001, under International Publication No. WO 01/56619 A1 and the disclosure of which is incorporated herein by reference.

BACKGROUND OF THE INVENTION

The present invention relates to liquid air freshener and insecticidal compositions, particularly those which can be evaporated from a container through a wall such as a membrane.

Air freshener and insecticidal compositions are well-known. These are used to fragrance or deodorize an environment or to control insects. Such compositions have traditionally been in solid form, but now may be in liquid, including thickened liquid or gelled, form. The liquid is generally held in a chamber.

The chamber may have a wicking arrangement such that the composition is evaporated from a wall which is in the form of a porous surface. Alternatively, the chamber may have at least one wall of a material that is permeable to the vapors of the composition, thereby allowing controlled release of the vapors over a period of time. Such an arrangement is described in U.S. Pat. No. 4,534,509, in which the fragrance is enclosed in an impermeable bag with a weak seal along one edge, which prevents escape of the vapors as long as the package is sealed. This is then contained within a larger pouch of a suitable permeable membrane. When sufficient pressure is applied by the user, the weak seal ruptures and the volatile composition flows from the inner pouch into the outer permeable pouch, thereby allowing release of the vapors.

An alternative arrangement is described in U.S. Pat. No. 4,634,614 in which the permeable wall is covered with a thin layer of paper coated with a polymer sheet to which adheres a protective sheet which is impermeable to the vapors of the composition. The paper layer tears when subjected to a peeling force such that the protective layer is readily removed and the volatile substance is covered only by a layer of material which is permeable to the vapors, thereby allowing release of the vapors.

A similar arrangement is described in International Patent Publication WO 98/23304 which comprises a membrane laminate having a plurality of layers. The outer layers of the laminate are impermeable to the composition and its vapors, and thus prevent escape of the vapors as long as the package is sealed. Upon opening, delamination occurs at the interface between two selected layers of the laminate, such that the composition is covered only by a layer of the material which is permeable to the vapors of the composition.

In such devices severe constraints are placed on the composition contained within the chamber. In particular, it must be able to evaporate satisfactorily through the wall relatively constantly throughout the life of the device. The device must also be storable for a long time without the composition affecting the properties of the wall or other parts of the chamber. Furthermore, the rate of evaporation of the composition must be controllable by the manufacturer such that a suitable lifetime of the device can be provided, which is generally of the order of about 45 days. It is desirable that after approximately this period, a suitable end of life indicator is provided so that the consumer can see when it is appropriate to buy a new device or refill composition for such a device. Suitable indication means are, for example, a significant visible reduction in the amount of the composition in the device, a change in color of the composition, or a change in form of the composition, for example from a liquid to a non-flowing gel.

In prior art devices of the type in which a composition is always in contact with the wall of a chamber and evaporates out of the chamber through said wall, there is a relatively small amount, for example about 3 g, of the composition present. In order to provide effective fragrancing for a lifetime of about 45 days, the composition must have a high concentration of fragrance with consequently only a small amount of solvent present. The solvent is chosen such as to aid diffusion of the fragrance through the wall of the chamber. A non-polar solvent is generally used since such a solvent has good diffusion properties through such walls.

It is now desired to produce such devices which may contain a greater quantity of liquid composition since some consumers regard this as beneficial. In order to obtain appropriate fragrancing or insecticidal properties under ambient conditions (i.e. at room temperature), it is not possible simply to increase the amount of composition present because this will increase the lifetime of the device. This may not be desirable when a lifetime of about 45 days is required. Furthermore, relatively constant fragrancing throughout the lifetime of device may not be achievable. Additionally, and more importantly, using a larger amount of the composition in the chamber will increase the amount of non-polar solvent present in the chamber. It has been found that such a quantity of non-polar solvent is sufficient to damage the wall during storage or use of the device, which will mean that the device will not function properly once it is opened or has been used for a short time. For example, if the wall is of the laminated membrane type, the membrane may suffer delamination.

It is not possible simply to replace the non-polar solvent with a polar solvent. Polar solvents are known to have poorer evaporation characteristics through membranes, and in particular will not normally pass through membrane walls of the type used in air freshener or insecticidal devices.

It is also desirable that a suitable end-of-life indication be provided for devices of this type so that the consumer can see when it is appropriate to buy a new device or refill composition for such a device. Suitable indication means include the visible absence of any composition in the device. Thus, it is particularly desirable for the composition to be formulated such that no residue of the solvent remains. The end-of-life indication is then simply when all of the solvent of the composition has disappeared, i.e. has evaporated out of the device.

BRIEF SUMMARY OF THE INVENTION

A non-aqueous, single phase, non-thickened liquid air freshener or insecticidal composition having a flash point of greater than about 62° C. is provided. The composition comprises:

a) a polar solvent;

b) up to about 10 wt % of a non-polar aliphatic hydrocarbon solvent; and c) a fragrance or an insecticide.

DETAILED DESCRIPTION OF THE INVENTION

A composition has been discovered which can be used in larger quantities in an air freshener or insecticidal device which has the appropriate evaporation characteristics through a wall membrane, and which does not destroy or damage the wall during storage or use of the device. Particularly, by using a mixture of a particular polar solvent and a particular non-polar solvent, the evaporation characteristics of the composition can easily be controlled by the manufacturer by altering the relative proportions of the two components and by an appropriate choice of each component. In particular, in the present invention the amount of non-polar solvent in the composition is not too high and thus the membrane wall is not damaged or destroyed.

It is known that the polar solvent by itself does not easily pass through the permeable membrane walls of the types used in air fresheners and insecticide devices and therefore does not provide adequate evaporation characteristics. It has surprisingly been found that when it is used in conjunction with the non-polar solvent, the polar solvent will have appropriate characteristics to dissolve and evaporate with the fragrance or insecticide and will not damage or destroy the membrane wall. Therefore, using a combination of a polar solvent and a non-polar solvent will provide the composition with appropriate characteristics for use in an air freshening or insecticidal device having a wall through which the composition diffuses.

The polar solvent may be chosen from a wide range of solvents, such as glycol ethers. Desirably the glycol ether is a ($C_{1-4}$ alkyl)glycol($C_{1-4}$ alkyl) ether, di($C_{1-4}$ alkyl)glycol ($C_{1-4}$ alkyl)ether, ($C_{1-4}$ alkyl)glycol di($C_{1-4}$ alkyl)ether, di($C_{1-4}$ alkyl)glycol di($C_{1-4}$ alkyl)ether or tri($C_{1-4}$ alkyl)glycol($C_{1-4}$ alkyl) ether. The alkyl groups may have 1, 2, 3 or 4 carbon atoms and may be, for example, methyl, ethyl, n-propyl, i-propyl, n-butyl, i-butyl, s-butyl or t-butyl groups.

For example, the polar solvent may be 3-butoxypropan-2-ol, commercially available as Dowanol PnB™; propylene glycol monomethyl ether, commercially available as Dowanol PM™; tripropylene glycol methyl ether, commercially available as Dowanol TPM™; dipropylene glycol methyl ether, commercially available as Dowanol DPM™; dipropylene glycol dimethyl ether, commercially available as Proglyde™ DMM; dipropylene glycol n-propyl ether, commercially available as Dowanol DPnP™; dipropylene glycol mono n-butyl ether, commercially available as Dowanol DPnB™; tripropylene glycol mono n-butyl ether, commercially available as Dowanol TPnB™; or propylene glycol n-butyl ether.

A single polar solvent, or a mixture of two or more polar solvents, may be used.

The non-polar aliphatic hydrocarbon solvent may also be chosen from a wide variety of such solvents. Examples are linear, cyclic or branched hydrocarbons, including cycloparaffinic hydrocarbons. Preferred hydrocarbons are linear or branched alkanes such as $C_{8-18}$ alkanes, preferably $C_{9-16}$ alkanes, more preferably $C_{9-12}$ alkanes or $C_{11-15}$ alkanes. A single non-polar solvent, or a mixture of two or more non-polar solvents, may be used. Often, however, a mixture of hydrocarbons is used since it is not necessary to use a single hydrocarbon and separation of different hydrocarbons is costly.

Preferred non-polar solvents are mixtures of $C_{9-12}$ and $C_{11-15}$ alkanes such as those commercially available as Isopar G™, Isopar H™, Isopar J™, Isopar K™, Isopar M™, Isopar L™ and Isopar MB™, as well as mixtures of $C_{13-16}$ alkanes such as those commercially available as Isopar P™, and distillates commercially available as Isopar V™. Other preferred non-polar solvents are aliphatic hydrocarbons commercially available as Norpar 12™ and Norpar 15™, and cycloparaffinic hydrocarbons commercially available as Exxsol D60™, Exxsol D80™, Exxsol D100™, Exxsol D220™, Exxsol D230™, Exxsol D100s™, Exxsol D110™, Exxsol D120™ and Exxsol D140™.

The composition has a flash point of greater than about 62° C., preferably greater than about 70° C. This is to ensure that the composition is not a fire hazard in use. Individual components of the composition may have flash points of less than these temperatures, so long as the final composition meets this requirement. Desirably the flash point of each component is as high as possible. A correlation has been found between the flash point of a compound and its rate of evaporation relative to n-butyl acetate. Evaporation rates can be expressed on a scale in which n-butyl acetate has an evaporation rate of 100. A higher value means that the compound has a greater rate of evaporation, and a lower flash point. In general, the evaporation rate of the polar solvent for use in the composition is preferably less than about 100. The evaporation rate of the non-polar aliphatic hydrocarbon solvent in the combination is preferably less than about 16.

The composition desirably comprises at least about 15 wt % of the polar solvent, preferably about 15 to about 40 wt %, more preferably about 15 to about 30 wt % of the polar solvent based on the total weight of the composition. The composition comprises less than about 10 wt % of the non-polar aliphatic hydrocarbon solvent, preferably about 1 to about 10 wt %, more preferably about 3 to about 8 wt %, most preferably about 4 to about 7 wt %, based on the total weight of the composition. The weight ratio of the polar solvent to the non-polar solvent is desirably about 1:1 to about 6:1, more preferably about 2:1 to 5:1, and most preferably about 3:1 to about 4:1. The amounts of each component and the weight ratio are, of course, chosen to provide a composition with appropriate characteristics.

The composition also comprises a fragrance when it is to be an air freshener composition, or an insecticide when it is to be an insecticidal composition. Air freshener fragrances are well-known to those skilled in the art. Any air freshener fragrance or fragrance composition compatible with the membrane may be used. Some fragrance compositions also contain a polar or non-polar solvent falling within the definitions set out above, or compounds which have an air freshening or deodorizing effect but which also act as such a solvent Any such solvent or compounds in the fragrance composition which is added to the final composition is to be taken into account when calculating how much polar solvent or non-polar solvent is present in the final composition. In particular, it is important for the total content of non-polar aliphatic hydrocarbon solvent in the composition to be less than about 10 wt %. Any suitable insecticide can be used.

The fragrance is desirably present in an amount of about 50 to 80 wt % of the total composition, preferably about 60 to 75 wt %.

The composition may also comprise one or more optional components which are conventionally used in the art. For example, a dye or ultra-violet absorbing agent, such as dihydroxybenzophenone, may be included to stabilize the fragrance or dye if necessary.

The amount of composition which can be contained in the device is not limited. However, since the composition is compatible with membrane wall, a larger amount of composition can be held in the device than has previously been feasible. For example, about 5 g to about 50 g of composition can be used, preferably about 5 g to about 20 g, more preferably about 8 to about 10 g.

An air freshener or insecticidal device is also provided which comprises a chamber containing a composition as defined above, said chamber having at least one wall of a material which enables the vapors of the composition to diffuse into the environment in which the device is placed.

The wall is permeable such that it allows the fragrance or insecticide to diffuse into the environment. It may be made of any suitable material, for example polyethylene or paper. The wall may have another layer laminated to either or both surfaces thereof, for example a layer or layers made of a polymer such as polyethylene. The wall may, in particular, be that described in U.S. Pat. No. 4,634,614. Alternatively the wall may be that described in WO 98/23304. In the latter document there is described a wall in the form of a permeable polyethylene membrane. The wall preferably is thin so as to allow a suitable release rate of the composition. For example, the wall may have a thickness of about 20 to about 100 micrometers, preferably about 30 to about 70 micrometers, more preferably about 40 to about 60 micrometers.

In order to prevent the device from releasing fragrance or insecticide before it is used, the wall may be covered by an impermeable sheet which is removed before the device is used. For example, the sheet may simply be peeled off the wall or otherwise removed and discarded. The sheet may be made of, for example, a laminate such as polyethylene laminated with a metal such as aluminum. In WO 98/23304, the impermeable sheet is a laminate of polyethylene and ethylene-vinyl alcohol copolymer. Alternatively, a number of vents may be provided to allow for an adjustable release of the fragrance or insecticide.

This invention will best be further understood in connection with the following, non-limiting Examples.

EXAMPLE 1

Compositions containing a single polar or non-polar solvent or comprising a polar solvent and a non-polar solvent were tested in an air freshener device to determine their weight loss through a membrane over time.

The solvents chosen were as follows:

| Non-Polar Solvents (commercially available from Exxon) | |
|---|---|
| 1. Isopar M ™ | a mixture of $C_{11-15}$ iso-alkanes having a flashpoint of 79° C. and an evaporation rate of <1. |
| 2. Isopar L ™ | a mixture of $C_{11-15}$ iso-alkanes having a flashpoint of 67° C. and an evaporation rate of 3. |
| 3. Isopar P ™ | a mixture of $C_{13-16}$ iso-alkanes having a flashpoint of 109° C. and an evaporation rate of <1. |
| 4. Norpar 12 ™ | a mixture of aliphatic hydrocarbons derived from petroleum having a flashpoint of >66° C. and an evaporation rate of 1. |
| 5. Exxsol D60 ™ | a mixture of aliphatic cycloparaffinic hydrocarbons having a flashpoint of 63° C. and an evaporation rate of 2.5. |
| 6. Exxsol D80 ™ | a mixture of aliphatic cycloparaffinic hydrocarbons having a flashpoint of 75° C. and an evaporation rate of <1. |

| Polar Solvents (commercially available from Dow Chemicals) | |
|---|---|
| A. Dowanol PnB ™ | 3-butoxypropan-2-ol having a flashpoint of 63° C. and an evaporation rate of 7. |
| B. Dowanol PM ™ | propylene glycol monomethyl ether having a flashpoint of 31° C. and an evaporation rate of 70. |
| C. Dowanol DPM ™ | dipropylene glycol methyl ether having a flashpoint of 75° C. and an evaporation rate of 3. |
| D. Proglyde DMM ™ | dipropylene glycol dimethyl ether having a flashpoint of 65° C. and an evaporation rate of 80. |

The above evaporation rates were determined relative to n-butylacetate which has an evaporation rate of 100; the value for Proglyde DMM™ was calculated as the product of the molecular weight and the vapor pressure (mm Hg at 20° C.). A high flashpoint generally gives a low evaporation rate.

The above solvents were used singly or combined in weight ratios of 75:25, 50:50 and 25:75. 8 g of each of the compositions was sealed in thermoformed reservoirs having a membrane laminate of linear low density polyethylene and aluminum as described in WO 98/23304 on one side thereof. The devices were activated by peeling back the aluminum laminate layer to expose the membrane. The devices were stored at ambient conditions and the weight loss monitored over 15 days.

The following tables set out the weight loss percentages over time:

|  | 8 days | 1 days | 5 days |
|---|---|---|---|
| Non-polar Solvents | | | |
| 1. Isopar M | 14% | 19% | 24% |
| 2. Isopar L | 34% | 45% | 60% |
| 3. Isopar P | 2% | 3% | 3% |
| 4. Norpar 12 | 35% | 44% | 55% |
| 5. Exxsol D60 | 57% | 68% | 79% |
| Polar Solvents | | | |
| A. Dowanol PnB | 7% | 9% | 11% |
| B. Dowanol PM | 2% | 2% | 2.5% |
| C. Dowanol DPM | 2% | 3% | 3.5% |
| D. Proglyde DMM | 20% | 25% | 31% |

| Combination Polar/Non-Polar | Mixtures 75:25 | | | Mixtures 50:50 | | | Mixtures 25:75 | | |
|---|---|---|---|---|---|---|---|---|---|
| | 8 days | 11 days | 15 days | 8 days | 11 days | 15 days | 8 days | 11 days | 15 days |
| A:1 | | | | 28% | 35% | 42% | 16% | 20% | 26% |
| A:2 | 29% | 37% | 45% | 38% | 48% | 60% | 34% | 47% | 60% |
| A:3 | 45% | 59% | 75% | 11% | 15% | 20% | 8% | 10% | 12% |
| A:4 | 50% | 63% | 74% | 52% | 66% | 78% | 27% | 33% | 40% |
| A:5 | 56% | 67% | 77% | 42% | 54% | 66% | 28% | 32% | 38% |
| A:6 | 59% | 73% | 86% | 32% | 40% | 50% | 24% | 30% | 37% |
| B:1 | 25% | 31% | 39% | 29% | 38% | 49% | 20% | 26% | 33% |
| B:2 | 46% | 57% | 70% | 48% | 63% | 77% | 30% | 34% | 38% |
| B:3 | 12% | 16% | 20% | 12% | 17% | 21% | 11% | 16% | 20% |
| B:4 | 46% | 58% | 70% | 69% | 83% | 95% | 25% | 29% | 31% |
| B:5 | 69% | 81% | 89% | 72% | 85% | 89% | 33% | 38% | 41% |
| B:6 | 46% | 54% | 61% | 51% | 62% | 75% | 31% | 39% | 46% |
| C:1 | | | | 23% | 30% | 38% | 28% | 34% | 42% |
| C:2 | 58% | 70% | 85% | 36% | 47% | 56% | 19% | 23% | 29% |
| C:3 | 12% | 17% | 21% | 12% | 16% | 20% | 8% | 10% | 12% |
| C:4 | 50% | 63% | 73% | 45% | 53% | 62% | 26% | 33% | 40% |
| C:5 | 40% | 51% | 60% | 63% | 78% | 86% | 50% | 52% | 56% |
| C:6 | 32% | 40% | 50% | 30% | 38% | 47% | 19% | 22% | 28% |
| D:1 | 28% | 36% | 46% | 41% | 52% | 66% | 20% | 27% | 33% |
| D:2 | 47% | 57% | 69% | 42% | 59% | 78% | 46% | 51% | 58% |
| D:3 | | | | 21% | 28% | 36% | | | |
| D:4 | 57% | 66% | 73% | 59% | 75% | 88% | 40% | 45% | 48% |
| D:5 | 69% | 81% | 89% | 68% | 85% | 95% | 44% | 58% | 71% |
| D:6 | 44% | 53% | 62% | 48% | 62% | 76% | 40% | 52% | 68% |

It can be seen that the weight loss can be controlled by choosing appropriate solvents and by choosing appropriate ratios of the two solvents.

EXAMPLE 2

A composition containing a fragrance was prepared to provide a composition for use in a membrane/liquid reservoir system having a fill weight of 9 g.

| Component | Weight Percent |
| --- | --- |
| Exxsol D60 ™ | 6 |
| Proglyde DMM ™ | 24 |
| Citrus fragrance | 68 |
| 2,4-dihydroxybenzophenone (u.v. absorber) | 2 |

The fragrance contained some polar solvent, namely 0.3% dipropylene glycol, 9.2% butoxypropanol and 0.9% triethyl citrate. The composition was sealed in the same device as used in Example 1, except that the membrane thickness was reduced from 60 micrometers to 40 micrometers.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. An air freshener or insecticidal device comprising a chamber containing about 5 to about 50 grams of a composition, wherein the chamber comprises at least one permeable membrane wall comprising a material which enables a vapor of the composition to diffuse through the wall and out of the chamber, and wherein the composition is a non-aqueous, single phase, non-thickened liquid air freshener or insecticidal composition having a flashpoint greater than about 62° C. and comprising:
   a) a polar solvent;
   b) a non-polar aliphatic hydrocarbon solvent, which is present in amount up to about 10 wt %, based on the total weight of the composition; and
   c) a fragrance or an insecticide;
wherein the polar solvent has an evaporation rate less than about 100 and the non-polar solvent has an evaporation rate less than about 16, both rates being based on a scale in which n-butyl acetate has an evaporation rate of 100.

2. The device according to claim 1, wherein the wall comprises a polyethylene.

3. The device according to claim 1, wherein the wall has a thickness of about 20 to about 100 micrometers.

4. The device according to claim 1, wherein the composition is an air freshener and comprises a fragrance.

5. The device according to claim 1, wherein the polar solvent comprises a glycol ether.

6. The device according to claim 5, wherein the polar solvent is selected from the group consisting of a ($C_{1-4}$ alkyl)glycol($C_{1-4}$ alkyl) ether, a di($C_{1-4}$ alkyl)glycol($C_{1-4}$ alkyl)ether, a ($C_{1-4}$ alkyl)glycol di($C_{1-4}$ alkyl)ether, a di($C_{1-4}$ alkyl)glycol di($C_{1-4}$ alkyl)ether, a tri($C_{1-4}$ alkyl)glycol($C_{1-4}$ alkyl) ether, and mixtures thereof.

7. The device according to claim 5, wherein the polar solvent is selected from the group consisting of 3-butoxypropan-2-ol, propylene glycol monomethyl ether, tripropylene glycol methyl ether, dipropylene glycol methyl ether, dipropylene glycol dimethyl ether, dipropylene glycol n-propyl ether, dipropylene glycol mono n-butyl ether, tripropylene glycol mono n-butyl ether, propylene glycol n-butyl ether, and mixtures thereof.

8. The device according to claim 1, wherein the non-polar solvent is a $C_{10-18}$ alkane or a cycloparaffinic hydrocarbon.

9. The device according to claim 1, wherein a weight ratio of the polar solvent to the non-polar solvent is about 1:1 to about 6:1.

10. The device according to claim 9, wherein the weight ratio is about 2:1 to about 5:1.

11. The device according to claim 1, wherein the non-polar solvent is present in an amount of about 1 to about 10 wt % based on the total weight of the composition.

12. The device according to claim 1, wherein the composition has an evaporation rate such that the device has a lifetime on an order of about 45 days.

13. The device according to claim 1, wherein the solvents of the composition leave no residue, thereby providing an end-of-life indication for the device.

14. The device according to claim 1, wherein the composition comprises:
   a) about 15 to about 40 wt % of the polar solvent;
   b) about 1 to about 10 wt % of the non-polar solvent; and
   c) about 50 to about 80 wt % of the fragrance or insecticide.

* * * * *